United States Patent [19]

Kersey

[11] Patent Number: 5,645,052
[45] Date of Patent: Jul. 8, 1997

[54] ANAESTHETIC VAPORIZER WITH EXPANDABLE/CONTRACTABLE RESERVOIR FOR PUMPING LIQUID ANAESTHETIC

[75] Inventor: Clifford Graham Kersey, Keighley, Great Britain

[73] Assignee: The BOC Group plc, Surrey, England

[21] Appl. No.: 587,063

[22] Filed: Jan. 16, 1996

Related U.S. Application Data

[63] Continuation of Ser. No. 137,210, filed as PCT/GB92/00752 Apr. 24, 1992 published as WO92/19303 Nov. 12, 1992, abandoned.

[30] Foreign Application Priority Data

Apr. 26, 1991 [GB] United Kingdom .................. 91 09021

[51] Int. Cl.[6] .......................... A61M 16/00; F23D 11/00; F23D 14/00; H05B 3/00
[52] U.S. Cl. ...................... 128/203.26; 128/203.12; 128/203.27; 128/203.16
[58] Field of Search .................. 128/203.12, 203.16, 128/203.17, 203.26, 203.27

[56] References Cited

U.S. PATENT DOCUMENTS

| | | | |
|---|---|---|---|
| 3,046,979 | 7/1962 | Andreasen | 128/205.16 |
| 3,789,837 | 2/1974 | Philips et al. | 128/203.26 |
| 4,010,748 | 3/1977 | Dobritz | 128/203.27 |
| 4,477,395 | 10/1984 | Albarda | 128/203.27 |
| 4,770,168 | 9/1988 | Rusz et al. | 128/203.27 |
| 5,243,973 | 9/1993 | Falb et al. | 128/203.27 |
| 5,277,175 | 1/1994 | Riggs et al. | 128/200.21 |

FOREIGN PATENT DOCUMENTS

| | | |
|---|---|---|
| 1104389 | 7/1984 | U.S.S.R. . |
| 2126666 | 3/1984 | United Kingdom . |

Primary Examiner—Kimberly L. Asher
Attorney, Agent, or Firm—Roger M. Rathbun; R. Hain Swope

[57] ABSTRACT

An anaesthetic vaporizer for supplying an anaesthetic to a patient and having an inlet for receiving carrier gas and an outlet for delivering carrier gas laden with the anaesthetic to the patient. The vaporizer includes a pump having an expandable body, preferably of a metal, and which expands to draw in the liquid anaesthetic from a reservoir through a valving mechanism and which collapses to meter a precise amount of that liquid anaesthetic into a chamber where it is vaporized for introduction into the carrier gas as it passes between the inlet and the outlet.

13 Claims, 3 Drawing Sheets

ANAESTHETIC VAPORIZER WITH EXPANDABLE/CONTRACTABLE RESERVOIR FOR PUMPING LIQUID ANAESTHETIC

This is a continuation of application Ser. No. 08/137,210 filed Oct. 25, 1993, now abandoned, which was a 371 of PCT/GB92/00752 filed Apr. 24, 1992, published as WO92/19303.

BACKGROUND OF THE INVENTION

This invention relates to an anaesthetic vaporiser. The vaporiser includes a pump for delivering a quantity of an anaesthetic agent accurately for administration to a patient.

It is generally necessary for anaesthetic agents to be delivered in accurately measured quantities over a period of time, for example, while the patient undergoes surgery.

As well as the requirement for accurate measurement of a dose of an anaesthetic agent, it can be desirable that a dosing pump in an anaesthetic vaporiser be capable of delivering quantities of the agent over a wide range of delivery rates. For example, the pump can be required to deliver the fluid at rates which vary by a factor of as much as 5500. For example, the rate of flow of carrier gas through the vaporiser might vary between 0.2 and 15 liters per minute, and the anaesthetic concentration might vary between 0.2 and 12% by volume.

A further problem which is encountered in the administration of anaesthetic agents is that such fluids are liable to degrade materials which are commonly used to provide fluid-tight seals in fluid handling equipment. Examples of such materials include many polymers such as that sold under the trade mark VITON Polymeric materials which are generally inert towards such fluids, such as polytetrafluoroethylene, are not generally able to provide an effective fluid-tight seal.

GB-A-2181493 discloses a pump for providing an accurately measured dose of an anaesthetic agent, which comprises a piston and a cylinder, each of which move within a housing by the action of respective eccentric drives. Movement of the piston and cylinder cause a fluid to be drawn into, and subsequently to be expelled from, a pump space. This pump suffers from the disadvantage that the pump space into which fluid is drawn is defined by components which can be moved relative to one another. Under certain operating conditions (generally involving fast operation of the pump to deliver a relatively large quantity of fluid), and when delivering certain aggressive fluids, degradation of the materials of seals provided between the moveable components can be subject to wear and then possibly to leakage of fluid from the pump space.

The present invention provides a vaporiser in which the pump which includes a reservoir for fluid defined by an expandable body.

SUMMARY OF THE INVENTION

Accordingly, in a first aspect, the invention provides an anaesthetic vaporiser which comprises an inlet for a carrier gas, an outlet for carrier gas and anaesthetic agent, and a pump for delivering a quantity of an anaesthetic agent into a stream of carrier gas, the pump comprising:

(a) a chamber having an inlet port, a reservoir port and an outlet port;

(b) a valve member which can be moved between a first position in which anaesthetic agent can flow through the chamber between the inlet port and the reservoir port, and a second position in which the agent can flow through the chamber between the reservoir port and the outlet port;

(c) a reservoir connected to the reservoir port in which the agent can be retained prior to delivery, the reservoir being defined by a resiliently expandable body; and (d) a drive unit by which the reservoir body can be expanded or contracted, to receive or to expel the agent respectively.

The vaporiser of the present invention has the significant advantage that fluids can be delivered which might otherwise degrade the materials of seals which might be used between moveable components defining a reservoir in which the anaesthetic agent is retained prior to delivery. Furthermore, the problem of leakage as a result of wear of a dynamic seal component is avoided. By forming the reservoir body from a material which has the resilience necessary for expansion, and which is inert towards the fluids to be delivered, the vaporiser of the present invention can be used to deliver a wide range of anaesthetic agents. By selection of a material for the reservoir body which has an appropriate ability to be deformed resiliently, the vaporiser of the present invention can be operated sufficiently quickly to deliver an agent at a high rate, such as is necessary in some applications. Furthermore, however, slow operation of the pump can then also provide a rate of delivery of agent which is at the lower end of the necessary range. A further advantage of the use of an expandable body of the reservoir is that the tendency for cavitation in the anaesthetic agent being drawn into the reservoir, which might be prevalent in piston and cylinder systems, is reduced, since the sub-atmospheric pressure caused by expansion of the reservoir body can be arranged to be progressive.

An appropriate reservoir body can be formed in the manner of a resiliently deformable bellows which is preferably closed at one end. Anaesthetic agent is received into the reservoir, and discharged from it, through the open end. The reservoir expands and contracts, to receive and to discharge anaesthetic agent respectively, by changing the axial length of the bellows. A reservoir body in the form of a bellows may be formed from a metal. A preferred metal is nickel, which has been found to be inert towards many anaesthetic agents. When the reservoir body is small, it can conveniently be formed by a deposition technique, for examples on a ceramic mould.

A further advantage of the use of a resiliently deformable body for the bellows is that it can return to its undeformed configuration after compression or expansion under its own force, and without the need for a return spring or other return mechanism.

In order to reduce fatigue of the materials of the reservoir body as a result of its deformation, it will be preferred generally that the body be deformed by a small amount from its relaxed condition. For example, a stainless steel bellows might be deformed through no more than about 18% of its axial length, preferably less than about 15% of its axial length, for example about 9% of its axial length.

It has been found to be particularly advantageous to reduce the amount of free volume within the reservoir. Furthermore, it can facilitate flushing of fluid from the reservoir since the amount of free fluid in the reservoir is thereby reduced. The free volume in the reservoir can be reduced by means of an appropriately shaped insert. For example, when the reservoir is provided by a reservoir body in the form of an axially deformable bellows, a length of a cylindrical tube with its ends closed, or of a rod, can be used to reduce the free volume in the reservoir. This can allow the free volume within the reservoir, when in its undeformed configuration, to be reduced by more than 50%, even more than about 85%.

Preferably, the drive unit by which the reservoir is expanded and contracted is provided by a stepper motor. Generally, a link will be provided between the drive unit and the reservoir. A preferred link is provided by a cam and a corresponding cam follower. Other forms of drive unit which might be used include, for example, a variable rate motor such as a variable rate DC motor. Other forms of link which might be used include an eccentrically driven arm, or a solenoid drive.

It is particularly preferred to use a stepper motor as the drive unit. It has been found that particular advantages arise from the use of such a drive unit. In particular, it has been found that the variation which can be achieved in the measured quantities of fluid dispensed from the reservoir can extend over a particularly wide range, making it possible for fluid to be dispensed in quantities which differ by a factor of as much as 5500. This is possible by operating the drive unit through incremental steps. Preferably the stepwise expulsion which takes place in each step-wise movement of the motor is less than about 5 μl, more preferably less than about 2 μl, particularly less than about 1 μl, for example less than about 0.7 μl. For example, a pump in a vaporiser according to the invention can be arranged to provide a flow rate of fluid of from $2 \mu l \, min^{-1}$ to $11000 \, \mu l \, min^{-1}$ by having stepwise expulsion of 0.33 μl. The range of flow rates is then arranged by appropriate adjustment of the speed of the stepper motor.

It has been found that the-use of a stepper motor as a drive unit has the special advantage that a high degree of resolution is available, which makes it possible to achieve a wide range of fluid flow rates, without needing to operate the reservoir through an expansion-contraction cycle at a high rate.

It can be preferred in many circumstances for the rates of reception and of expulsion of fluid respectively to differ. Generally, it will be preferred that the rate at which fluid is received in the reservoir will be very much greater than the rate which is expelled from it. Most preferably, the rate at which the reservoir is filled with fluid will be as fast as possible, while avoiding cavitation and other undesirable events. By arranging for the rate at which fluid is received in the reservoir to be as fast as possible, it is possible at all but the fastest flow rate to create an almost continuous rate of expulsion of fluid from the pump. This can be arranged in any of a number of ways: for example, the control unit of the stepper motor can be programmed to provide for different rates of movement, synchronised with the movement of the valve, this possibility arising from the use of a stepper motor making yet more advantageous the use of a stepper for the drive unit. The solenoid driven three-way valve may be selected for its ability to switch quickly. The cam in the link between the drive unit and the reservoir can be selected with a profile to provide different rate of filling and dispensing; for example, filling may take place over less than about 120° of rotation of the cam, for example about 90°, and dispersing may take place over at least about 220° of rotation, for example about 270°.

A continuous rate of expulsion of fluid can be simulated yet more accurately by arranging for the rate of flow of expelled fluid immediately after filling of the reservoir to be a small amount greater than that during normal expulsion to make up for the lost delivery during the filling cycle.

Characteristics of fluid flow into and out of the pump can be controlled by use of a cam with an appropriately selected profile. For example, the use of a profiled cam can be relied on to provide a rate of flow into the pump that is faster than the rate of outward flow, as referred to above.

In order that the variations in speed of expansion and contraction of the reservoir be timed accurately relative to the cycle of the pump, it is preferred that the pump includes means for detecting the degree of expansion of the reservoir. This can take the form of, for example, an opto-electronic device, which might be triggered, for example, when the reservoir reaches the maximum desired extent of expansion.

Generally, the pump will be used to direct a flow of an anaesthetic agent from a storage container to the breathing circuit of a patient. In this event, the inlet port of the chamber will be connected to the supply container for the agent, and the outlet port of the chamber will be connected to the patient's breathing circuit. In some situations, it can be preferable for the direction of flow to be reversed, for example to flush the fluid in question out of conduits connected to the outlet port. It is preferred that the cycle operated by the pump be capable of variation between two modes by varying the relative timing of the moveable valve member and the expansion and contraction of the reservoir. In this way, the flow of agent through the pump can be reversed.

Preferably, the vaporiser includes a monitor which can detect the presence of fluid in or absence of fluid from conduits attached to the inlet port of the chamber, the outlet port or both. The monitor can ensure that the pump of the vaporiser operates only when there is sufficient fluid for supply by the pump.

The valve member may be rotatable between its first and second positions. It will generally provide a bore in the plane perpendicular to the axis of rotation so that, in the first position of the valve member, the bore extends between the inlet port and the reservoir port, and so that, in the second position of the valve member, the bore extends between the reservoir port and the outlet port. While it is necessary to provide fluid-tight seals between the valve member and the chamber in which it moves, those seals have been found not to be susceptible to degradation as a result of movement in each cycle of the pump, unlike seals provided in reservoirs in earlier pumps, which consist of piston and cylinder arrangements. The range of movement of the valve member is somewhat less than that of a piston and cylinder type reservoir. Furthermore, and perhaps more significantly, the frequency with which the valve member must move can be arranged to be very much less than the frequency with which fluid is expelled from the reservoir by use of a drive unit which can expel incremental quantities of fluid from the reservoir.

A preferred valve member is a solenoid driven three way valve. It has been found that the use of such a valve has the advantage that the switching movement can be faster than that which can be achieved using a valve using rotational movement.

Preferably, the valve member is biased towards its first position so that, in the event of failure of a component of the pump of the vaporiser, it is not possible for fluid to flow from the reservoir through the outlet port of the chamber. This provides a measure of safety which can be important when, for example, the fluid is a drug.

During use, it is preferred that the pressure of the fluid at the inlet port is sufficiently high for the agent to be maintained in its liquid phase. It is further preferred that the pressure is so maintained at all stages through the pump, as far as the point where the fluid is delivered from the pump. In this way, the accuracy with which the pump is able to measure fluid volumes can be maintained high even with fluids such as high boiling point anaesthetic agents. An anaesthetic agent of particular interest which has been developed recently, 2-(difluoromethoxy) 1,1,1,2-tetrafluoroethane, has a boiling point at normal atmospheric pressure between 20° and 25° C., while normal operating temperatures of the vaporiser of the invention can be between 15° and 35° C. Maintaining the pressures of the agent in the vaporiser at such levels that it remains in its liquid phase allows the pump in the vaporiser of the invention to measure volumes of that drug accurately.

The vaporiser of the invention includes an inlet for a carrier gas, and an outlet for carrier gas and anaesthetic agent. The pump supplies anaesthetic agent into the carrier gas stream, in accurately measured quantities. A suitable vaporiser is disclosed in the application, filed with the present application, which claims priority from UK patent application no. 9109023.3. Subject matter disclosed in that application is incorporated in the specification of the present application by this reference.

BRIEF DESCRIPTION OF THE DRAWINGS

A vaporiser in accordance with the present invention will now be described by way of example, with reference to the accompanying drawings, in which.

DESCRIPTION OF THE PREFERRED EMBODIMENT

Figure 1:
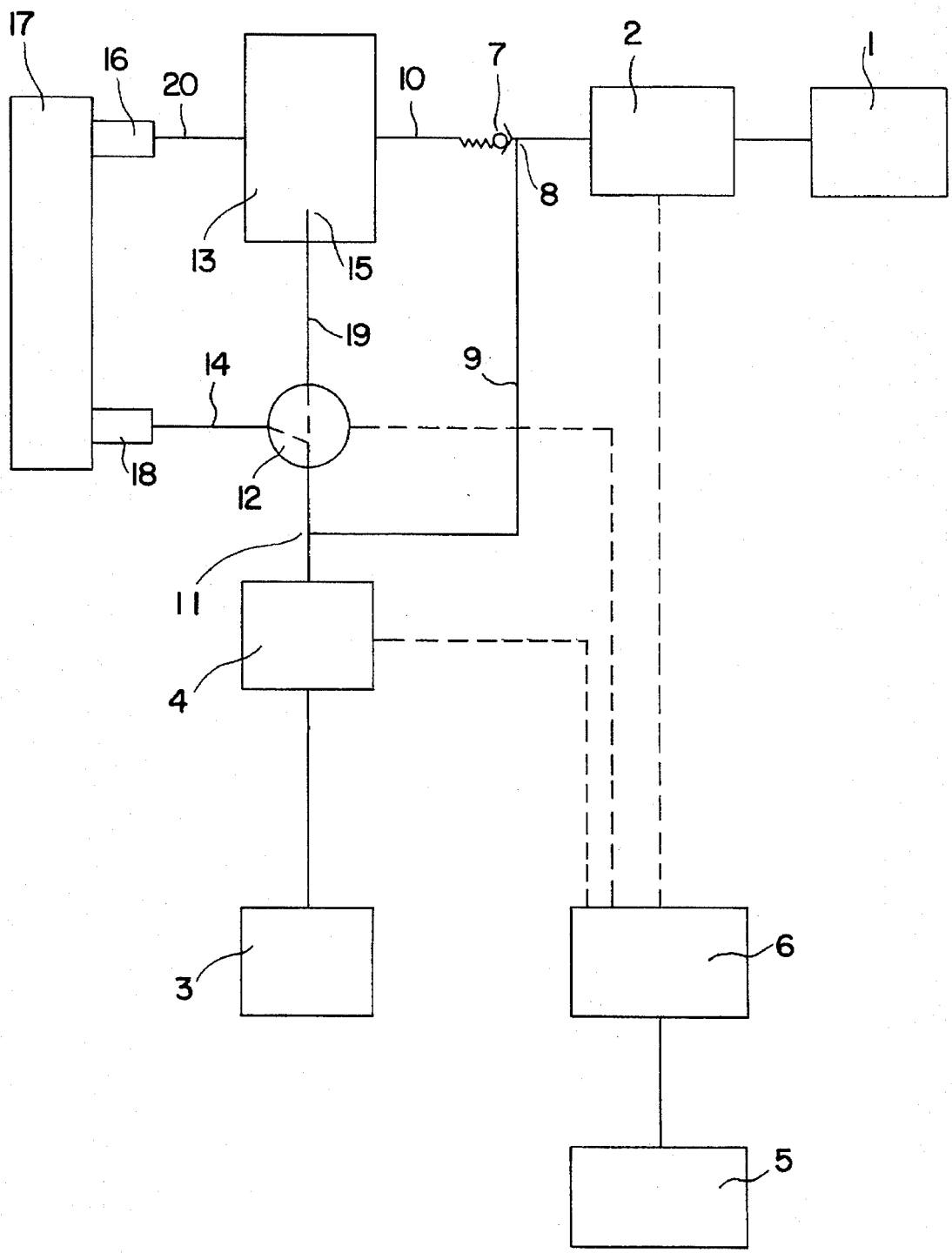
FIG. 1 is a schematic representation of a vaporiser.

Referring to the drawings, FIG. 1 shows a vaporiser which comprises a source 1 of a carrier gas, which might consist of, for example nitrous oxide, oxygen or air, or a combination of these gases. The carrier gas flows from the source 1 through a flow sensor 2, which allows the rate of flow of carrier gas to be monitored.

A back pressure regulator 7 is situated downstream of the flow sensor 2 to control the split of carrier gas at a junction 8 between a first passageway 9 and a second passageway 10. The regulator 7 ensures that no more than a predetermined quantity of gas flows through the first passageway 9, excess gas being admitted to the second passageway 10. Liquid drug, for example an anaesthetic drug, is held in a reservoir 3, and is supplied to the first passageway 9 through a dosing pump 4 by which the rate of supply of the drug is controlled, according to the required concentration of drug and the required rate of flow of gas into the patient's breathing circuit.

The overall control of the dosing pump 4 to introduce the proper desired amount of liquid anaesthetic into the eventual anesthetic/carrier gas delivered to the patient circuit 17 may be controlled by a controller 6 which receives a signal from the flow sensor 2 indicative of the overall flow of carrier gas entering the vaporizer, and therefore can control the speed of the dosing pump 4 to set the desired concentration set by the user through some user input 5, such as a keyboard, dial or the like. In addition, the controller 6 may exercise control of the position of the switch 12 depending, again, on the concentration of anesthetic that the user desires to be administered to the patient circuit 17.

Figure 3:
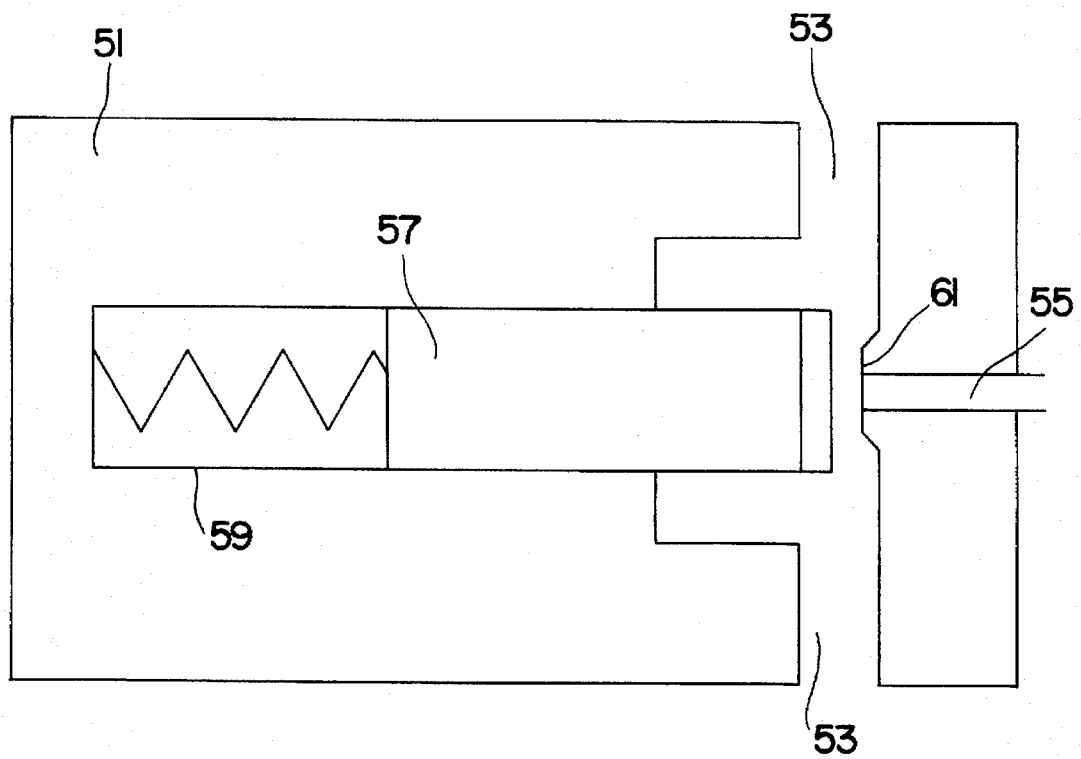
FIG. 3 is a schematic representation of a back-pressure valve which might be Us anaesthetic he flow of anaesthetic agent from a reservoir.

When the pump is used to deliver an anaesthetic agent having a boiling point similar to ambient temperature, such as 2-(difluoromethoxy) -1,1,1,2-tetrafluoroethane, the agent is supplied from a pressurised reservoir. A back pressure valve, which might consist of a ball and spring, or be as shown in FIG. 3 below, is placed in the delivery line at the junction 11 where drug from the reservoir enters the first passageway 9, and is set to cause a pressure to be developed in that line. A pressure of approximately 5 g.mm$^{-2}$ can ensure that the agent referred to above remains in is liquid phase at operating temperatures of the valve up to about 35° C.

Drug supplied from the reservoir 3 enters the first passageway 9 at junction 11, and the resulting mixture of carrier gas and drug then flows to a switch 12 by which the subsequent flow of the gas and drug can be selected between a first sub-passageway 19 which conducts the gas and liquid to a mixing chamber 13, and a second sub-passageway 14 through which the drug and carrier gas are administered to the breathing system 17 of a patient, via an outlet 18. The first sub-passageway 19 conducts the carrier gas and drug to mixing chamber 13 through a nozzle 15 which ensures atomisation of the liquid drug, where it is diluted with excess gas flow which flowed from the regulator 7 through the second passageway 10, leading also to the mixing chamber 13. A third passageway 20 leads directly from the mixing chamber 13 to an outlet 16, through which carrier gas from the first and second passageways 9, 10, and drug, can be administered to the breathing system 17 of a patient.

Figure 2:
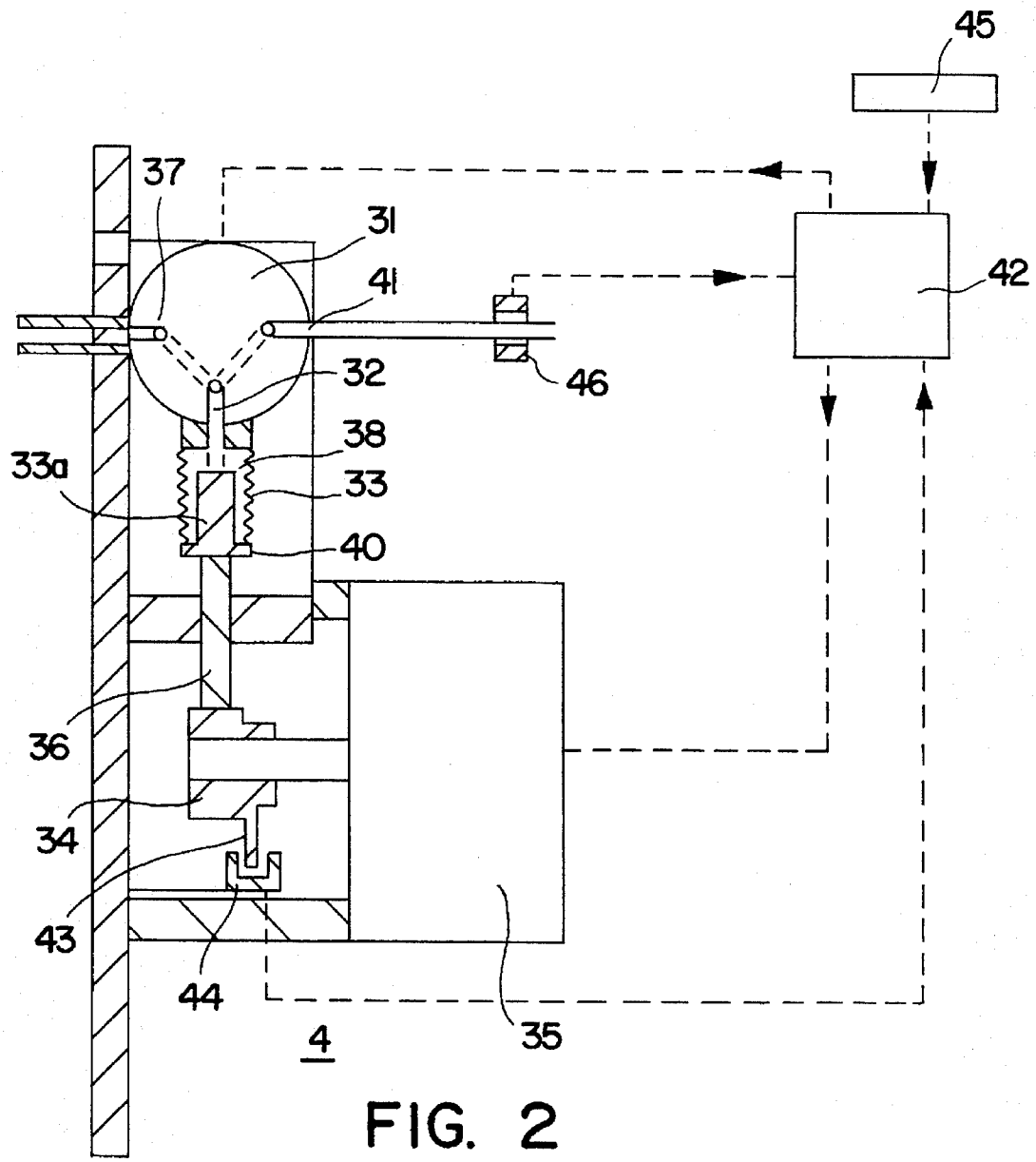
FIG. 2 a schematic representation of a pump.

FIG. 2 shows the dosing pump 4 of the vaporiser of FIG. 1, which consists of a three-way valve 31. A reservoir port 32 is connected to a reservoir body in the form of a bellows composed of a metal such as nickel 33. The bellows 33 is acted on by a cam follower 36 at which acts against a cam 34 driven by a stepper motor 35.

The inlet port 37 of the three-way valve 31 is connected to a container for a drug. The outlet port 41 of the three-way valve 31 is connected to a conduit through which the fluid drug is supplied to a patient.

The bellows 33 contains an insert 33a by which the free volume of the bellows is reduced.

A control unit 42 determines the speed of the stepper motor 35. Again, a patient input 45 may be used to enable the user to select the desired anaesthetic concentration to be delivered to the patient. Information on the position of the cam 34 and of the bellows 33 is provided by a flag 43 attached to the cam 34, which passes through an optical-interrupting device 44.

A further optical-interrupting device 46 is provided on the output line, and senses the presence of liquid in the output line.

Operation of the pump is as follows. While the cam 34 is at the top of its stroke, the bellows 33 is compressed axially. At this stage, the three-way valve 31 is arranged so that a passage way extends from the inlet port 37 to the reservoir port 32. As the cam 34 rotates, the bellows 33 begins to expand under its own resilient spring force. This has the advantage of minimising cavitation in fluid in the bellows, which has been found to be exacerbated when the bellows are expanded under externally applied force. As the bellows 33 expands, liquid is drawn into the cavity 38 created within the bellows, between the top of the bellows 33, the bottom 40 of the bellows and the bellows insert 33a. Liquid continues to be drawn into the bellows until the cam 34 reaches the bottom of its stroke. The valve 31 is then switched so that fluid can flow from the reservoir port 32 to the outlet port 41. The bellows 33 is then forced to contract axially as a result of upward force exerted by the cam 34 and cam follower 36, driving fluid out of the cavity through the outlet port 41.

The control Unit 42 controls the speed of the stepper motor so that it moves quickly while the bellows expands. The speed at which the bellows contracts is selected according to the desired rate of fluid out of the pump.

FIG. 3 shows a back pressure valve which might be used to control the flow of anaesthetic agent from a reservoir where it is stored under pressure. The valve comprises a housing 51 with a first bore 53 extending through it for carrier gas. Anaesthetic agent enters the first bore through a second bore 55. The junction between the first and second bores can be closed by means of a spring loaded plunger 57, which slides within a tubular chamber 59, into contact with a seat 61 to close the second bore.

The ability of the vaporiser of the invention to dispense fluids over a wide range of flow rates has the advantage that it can be used to dispense a range of anaesthetic agents. Such agents can be required to be dispensed over a wide of range of flow rates, differing by a factor of as much as 5500, depending on the agent in question and on the conditions under which it is administered to a patient.

Volumes and other design aspects of a design of pump are given as follows:

Volume of the reservoir: 450 µl

Free volume of the reservoir: 350 µl

Volume of fluid discharged per revolution of the cam: 100 µl

Volume of fluid discharged per step: 0.33 µl

Filling time: 0.1 s

Motor rotation rate: 0.02 to 122 rev.min$^{-1}$

Discharge time per step: 0.0013 to 9 s

I claim:

1. An anaesthetic vaporizer which comprises an inlet for receiving a carrier gas, an outlet for discharging carrier gas and anaesthetic agent, and a vaporizing chamber intermediate the inlet and the outlet wherein liquid anaesthetic agent is vaporized into the stream of carrier gas, the improvement comprising a pump for delivering a quantity of an anaesthetic agent into said vaporizing chamber, said pump comprising:
    (a) a chamber having an inlet port for connection to a supply of liquid anaesthetic, a reservoir port and an outlet port fluidly connected to said vaporizing chamber;
    (b) a valve member which can be moved between a first position in which the anaesthetic agent can flow from the supply of liquid anaesthetic through the chamber between the inlet port and the reservoir port, and a second position in which the agent can flow through the chamber between the reservoir port and the outlet port;
    (c) a reservoir connected to the reservoir port in which the agent can be retained prior to delivery, the reservoir being defined by a flexible, expandable body;
    (d) a drive unit connected to said reservoir body to expand said reservoir body to draw liquid anaesthetic from the supply of liquid anaesthetic through said valve member or to contract said reservoir body to force anaesthetic agent from said reservoir through said valve member to said vaporizing chamber; and
    (e) a control unit controlling said drive unit to expand said reservoir body at an independently selected rate to draw a predetermined amount of the liquid anaesthetic and to contract said reservoir body at an independently selected rate to force a predetermined quantity of liquid anaesthetic to said vaporizing chamber.

2. A vaporiser as claimed in claim 1, in which the reservoir body is formed in the manner of a resiliently deformable bellows.

3. A vaporiser as claimed in claim 2, in which the bellows is closed at one end.

4. A vaporiser as claimed in claim 2, in which the drive unit and the bellows are arranged so that the maximum degree of deformation of the bellows during an expansion and contraction cycle is less than about 18% of its axial length measured in the relaxed condition of the bellows.

5. A vaporiser as claimed in claim 2, includes means for detecting the degree of expansion of the reservoir.

6. A vaporiser as claimed in claim 1, which includes an insert within the reservoir body, by which the free volume of the reservoir is reduced.

7. A vaporiser as claimed in claim 1, in which the drive unit by which the reservoir is expanded and contracted comprises a stepper motor.

8. A vaporizer as claimed in claim 1, which includes a cam and a cam follower between the drive unit and the reservoir for expanding and contracting said reservoir.

9. A vaporiser as claimed in claim 1, in which the valve is rotatable between its first and second positions.

10. A vaporiser as claimed in claim 9, in which the valve member is biassed towards its first position.

11. A vaporiser as claimed in claim 1, which includes a monitor which can detect the presence of fluid in or absence of fluid from conduits attached to the inlet port of the chamber, the outlet port or both.

12. An anaesthetic vaporizer which comprises an inlet for receiving a carrier gas, an outlet for discharging carrier gas and anaesthetic agent, and a vaporizing chamber intermediate the inlet and the outlet wherein liquid anaesthetic agent is vaporized into the stream of carrier gas, the improvement comprising a pump for delivering a quantity of an anaesthetic agent into said vaporizing chamber, said pump comprising:
    (a) a chamber having an inlet port for connection to a supply of liquid anaesthetic, a reservoir port and an outlet port fluidly connected to said vaporizing chamber;
    (b) a valve member which can be moved between a first position in which the anaesthetic agent can flow from the supply of liquid anaesthetic through the chamber between the inlet port and the reservoir port, and a second position in which the agent can flow through the chamber between the reservoir port and the outlet port;
    (c) a reservoir connected to the reservoir port in which the agent can be retained prior to delivery, said reservoir having an expandable body comprising of a resiliently deformable metal bellows; and
    (d) a drive unit by which the reservoir body can be expanded to draw liquid anaesthetic from the supply of liquid anaesthetic through said valve member or contracted to force anaesthetic agent from said reservoir through said valve member to said vaporizing chamber.

13. An anaesthetic vaporizer which comprises an inlet for receiving a carrier gas, an outlet for discharging carrier gas and anaesthetic agent, and a vaporizing chamber intermediate the inlet and the outlet wherein liquid anaesthetic agent is vaporized into the stream of carrier gas, the improvement comprising a pump for delivering a quantity of an anaesthetic agent into said vaporizing chamber, said pump comprising:
    (a) a chamber having an inlet port for connection to a supply of liquid anaesthetic, a reservoir port and an outlet port fluidly connected to said vaporizing chamber;

(b) a valve member which can be moved between a first position in which the anaesthetic agent can flow from the supply of liquid anaesthetic through the chamber between the inlet port and the reservoir port, and a second position in which the agent can flow through the chamber between the reservoir port and the outlet port;

(c) a reservoir connected to the reservoir port in which the agent can be retained prior to delivery, the reservoir being defined by a flexible, expandable body; and (d) a drive unit by which the reservoir body can be expanded to draw liquid anaesthetic from the supply of liquid anaesthetic through said valve member or contracted to force anaesthetic agent from said reservoir through said valve member to said vaporizing chamber; and (e) cam and a cam follower between said drive unit and said reservoir for expanding and contracting said reservoir, and wherein said cam is configured such that the rate at which the agent is received into said reservoir is significantly greater than the rate at which liquid is expelled from said reservoir.

* * * * *